United States Patent [19]

Merger et al.

[11] Patent Number: 4,611,079

[45] Date of Patent: Sep. 9, 1986

[54] PROCESS FOR THE PREPARATION OF N-ARYL DI- OR POLYURETHANES

[75] Inventors: Franz Merger, Frankenthal; Friedrich Towae, Ludwigshafen, both of Fed. Rep. of Germany

[73] Assignee: BASF Aktiengesellschaft, Ludwigshafen, Fed. Rep. of Germany

[21] Appl. No.: 619,562

[22] Filed: Jun. 11, 1984

Related U.S. Application Data

[63] Continuation-in-part of Ser. No. 542,824, Oct. 17, 1983, abandoned, which is a continuation of Ser. No. 135,304, Mar. 31, 1980, abandoned.

[30] Foreign Application Priority Data

Apr. 30, 1979 [DE] Fed. Rep. of Germany ....... 2917569

[51] Int. Cl.$^4$ ............... C07C 125/073; C07C 125/077
[52] U.S. Cl. ........................ 560/25; 560/21; 560/22
[58] Field of Search ....................... 560/24, 25, 27, 28, 560/29, 30, 31, 32, 21, 22

[56] References Cited

U.S. PATENT DOCUMENTS

| | | |
|---|---|---|
| 2,191,663 | 11/1939 | Martin . |
| 2,343,808 | 3/1944 | Schlack . |
| 2,409,712 | 10/1946 | Schweitzer ........................ 560/24 |
| 2,568,885 | 9/1951 | Dreyfus . |
| 2,623,867 | 12/1952 | Dreyfus . |
| 2,653,144 | 9/1953 | Wielicki . |
| 2,806,051 | 9/1957 | Brockway ........................ 560/24 |
| 2,817,684 | 12/1957 | Bortnick . |
| 2,828,291 | 3/1958 | Saunders . |
| 2,973,342 | 2/1961 | Inaba et al. . |
| 3,046,254 | 7/1962 | Imaba et al. . |
| 3,054,777 | 9/1962 | Imaba et al. . |
| 3,054,819 | 9/1962 | Barclay, Jr. et al. ........... 260/453 P |
| 3,119,793 | 1/1964 | Imaba et al. . |
| 3,185,656 | 5/1965 | Gabler et al. . |
| 3,223,682 | 12/1965 | Gablet et al. . |
| 3,291,763 | 12/1966 | Becalick et al. . |
| 3,366,662 | 1/1968 | Kober et al. ................... 260/453 P |
| 3,388,103 | 6/1968 | Imohl et al. . |
| 3,390,137 | 6/1968 | Kirshenbaum et al. . |
| 3,412,072 | 11/1968 | Bouboulis et al. . |
| 3,461,149 | 8/1969 | Hardy et al. .................... 260/453 P |
| 3,467,687 | 9/1969 | Hardy et al. .................... 260/453 P |
| 3,467,688 | 9/1969 | Bennett et al. .................. 260/453 P |
| 3,481,967 | 12/1969 | Ottmann et al. ................ 260/453 P |
| 3,523,962 | 8/1970 | Ottmann et al. ................ 260/453 P |
| 3,574,711 | 4/1971 | Robeson ............................. 560/157 |
| 3,734,941 | 5/1973 | Sydor ............................. 260/453 P |
| 3,763,217 | 10/1973 | Brill . |
| 3,895,054 | 7/1975 | Zajacek et al. . |
| 3,992,430 | 11/1976 | Bacskai ........................ 260/453 P X |
| 4,081,472 | 3/1978 | Tsumura ........................ 260/453 P |
| 4,153,624 | 5/1979 | Fern ............................. 260/453 P |
| 4,260,781 | 4/1981 | Harvey ............................. 560/24 |
| 4,310,692 | 1/1982 | Findeisen et al. ................. 564/61 |
| 4,388,238 | 6/1983 | Heitkamper et al. ............. 560/24 X |
| 4,398,036 | 8/1983 | McCoy ............................. 560/25 |
| 4,430,505 | 2/1984 | Heitkamper et al. ............. 560/24 |

FOREIGN PATENT DOCUMENTS

| | | |
|---|---|---|
| 528437 | 5/1938 | United Kingdom . |
| 530267 | 6/1938 | United Kingdom . |
| 1025436 | 8/1964 | United Kingdom . |

OTHER PUBLICATIONS

Sandler et al., Organic Functional Group Preparations, vol. (II) (1971), 235-239, 244 & 245.

*Primary Examiner*—Bernard Helfin
*Attorney, Agent, or Firm*—William G. Conger; Joseph D. Michaels

[57] ABSTRACT

A method for the production of N-aryl substituted di- and polyurethanes in high yield, by the reaction of an aromatic di- or polyamine with urea and alcohol at high temperatures. The di- and polyurethanes thus produced have utility as isocyanate precursors.

18 Claims, No Drawings

PROCESS FOR THE PREPARATION OF N-ARYL DI- OR POLYURETHANES

This is a continuation-in-part of copending application Ser. No. 542,824, filed Oct. 17, 1983, now abandoned, which is a continuation of application Ser. No. 135,304, filed Mar. 31, 1980, now abandoned, which claims priority to Federal Republic of Germany application Ser. No. 2917569, filed Apr. 30, 1979.

1. FIELD OF THE INVENTION

The subject invention relates to a process for the preparation of N-aryl-substituted carbamic acid esters, or N-aryl urethanes. More particularly, the process involves the preparation of N-aryl-substituted di- or polyurethanes by reacting aromatic di- or polyamines with urea and excess alcohol. The N-aryl-substituted di- and polyurethanes are particularly useful as di- and polyisocyanate precursors.

2. BACKGROUND OF THE INVENTION

Large quantities of di- and polyisocyanates are produced each year. The largest part of isocyanate production is destined for the preparation of urethane group-containing polymers, especially cellular and non-cellular polyurethanes. Several isocyanates are produced commercially but by far the largest quantities are mixtures of 2,4- and 2,6-toluene diisocyanates, and the various isomers of diphenylmethane diisocyanate and their mixtures, plus its higher polymeric homologs (polymeric MDI). Since the first isocyanate synthesis by Wurtz in 1854 in which methyl isocyanate was produced from dimethylsulfate and potassium cyanate, many methods have been developed for the production of isocyanates. However, the only commercially feasible method has been the phosgenation of amines or amine salts, a reaction practiced by Hentschel at least as early as 1884.

The industrial process for the production of isocyanates suffers from several major disadvantages. Central to these disadvantages is the use of phosgene. Phosgene is exceptionally toxic and corrosive making its handling hazardous. Furthermore, the manufacture of phosgene, often performed on site, is also hazardous, as it involves the reaction of carbon monoxide with chlorine. The necessity of having a captive supply of chlorine available makes phosgene production expensive, due to the high cost of electricity used in the preparation of chlorine. The cost of chlorine production is also subject to severe market fluctuation because of the necessity to sell or otherwise dispose of large amounts of caustic or its equivalents. In addition to these disadvantages relative to the cost, danger and difficulty of handling, the use of phosgene suffers from another disadvantage in that two moles of by-product hydrogen chloride are produced per mole of isocyanate group formed. This large amount of hydrogen chloride, generally in the form of the acid, must be recycled, sold or disposed of as waste.

Because of the foregoing disadvantages of the phosgene process for isocyanate production, there has been a long-felt need for a phosgene-free method. This need was expressed more than 25 years ago in U.S. application No. 757,907 of 1958, which matured into U.S. Pat. No. 3,054,819 on Sept. 18, 1962. The patentees indicated that several non-phosgene processes had been developed but that none had met with commercial success. In particular, the thermal cleavage of N-substituted carbamic acid esters was discussed. While phosgene was not necessary to prepare isocyanates from N-substituted carbamates, unfortunately, phosgene was necessary to prepare the carbamates themselves. Thus, the use of phosgene was not eliminated but merely shifted to an earlier process step. The process of U.S. Pat. No. 3,054,819 involved the pyrolysis of N-substituted carbamates formed by reaction of an amine with diethylcarbonate. However, as with the industrial preparation of N-substituted carbamates, the manufacture of diethylcarbonate also requires the use of phosgene. Thus again the use of phosgene is not eliminated but merely shifted to another process step.

In U.S. Pat. No. 3,467,687 an aromatic nitroso compound is reacted with carbon monoxide in the presence of a suitable catalyst to produce isocyanates. However, this process requires high pressure and the use of both noble metal and Lewis acid catalysts. Furthermore, while eliminating the use of phosgene and its attendant disadvantages, the process does involve the use of carbon monoxide, itself a highly poisonous and corrosive gas. Because of these difficulties, this process has not been commercialized.

Several processes have been developed utilizing the reaction of carbon monoxide with an aromatic nitro compound. Illustrative is U.S. Pat. No. 3,481,967, patented Dec. 2, 1967. While this process suffers from the same disadvantage of the use of carbon monoxide as previously discussed, an advantage is the avoidance of the necessity to reduce the aromatic nitro compound to the corresponding amine. Hence, this process would appear to have some attractive economic advantages. Unfortunately, the separation of toxic catalysts (generally selenium in the modern versions of this process) from the product has proven difficult. Hence, this process also has not been utilized commercially.

A commercially feasible, non-phosgene process for the production of isocyanates, therefore, has thus far eluded the chemical industry. It is an object of this invention to enable the non-phosgene production of isocyanates through the preparation of N-aryl substituted carbamate esters (hereinafter N-aryl urethanes) in high yield, by a process which does not involve phosgene or carbon monoxide in any step. Nor does the process involve the use of highly toxic metals as catalysts. These N-aryl urethanes may then be thermally cleaved to isocyanates by known processes as, for example, described in U.S. Pat. No. 3,919,278.

DESCRIPTION OF THE PRIOR ART

N-aryl mono- and diurethanes are prepared industrially by (a) the reaction of alcohols with isocyanates, or (b) the reaction of amines with chlorocarbonates. For example, N-phenyl urethane may be prepared as illustrated below.

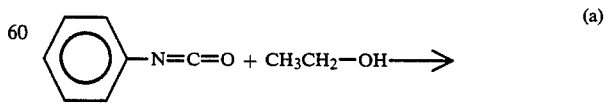

(a)

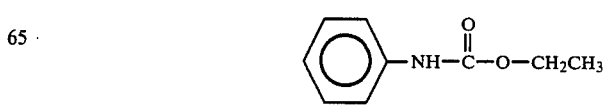

-continued

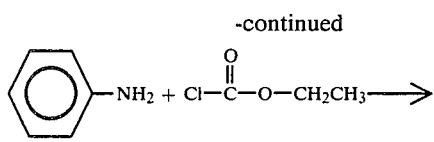

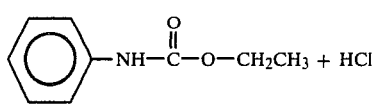

Both of these methods involve the use of phosgene either in production of the initial isocyanate or the production of the chlorocarbonate. German published application No. 2 160 111 describes a process similar to (b), above, for the manufacture of N-substituted monourethanes, by reacting an organic carbonate with a primary or secondary amine in the presence of a Lewis acid. However, this process involves long reaction times, suffers from rather low yields, and always produces N-alkylarylamines as by-products. Furthermore, the industrial preparation of diethylcarbonate and other carbonates still involves the use of phosgene.

U.S. Pat. No. 2,834,799 describes a process for making carbamic and carbonic esters by the reaction of urea with alcohols in the presence of boron trifluoride. A disadvantage of this method is that boron trifluoride is required in equi-molar quantities so that at least one mole of boron trifluoride is used per mole of carbamic ester produced, and at least two moles of boron trifluoride are consumed per molecule of carbonic ester. This process, therefore, is not only expensive but causes serious environmental problems due to the production of the $H_3N \cdot BF_3$ adduct.

R. A. Franz et al, *Journal of Organic Chemistry*, 28, page 585 (1963), describe a process for making methyl N-phenyl urethane from carbon monoxide, sulfur, aniline, and methanol. However, very low yields are produced by this method; the yield does not exceed 25 percent even when there is a long reaction period.

U.S. Pat. No. 2,409,712 describes the preparation of N-alkyl and N-aryl monourethanes wherein the esterifying alcohol is an aliphatic alcohol, an alkoxyalkanol, or an alkoxyalkoxyalkanol. The ratio of amine to urea to alkanol is approximately 1:1:1 to 1:1:3 and the yields are rather low, ca. 50 to 60 percent. Furthermore, it appears that the reaction is far from general as the N-isobutyl and N-phenyl carbamates were prepared by reacting N,N'-diisobutylurea and N,N'-diphenylurea with an alcohol to produce the respective N-substituted monourethanes. It further appears that aromatic amines are not very reactive under the reaction conditions cited, as aniline was able to be distilled from the N,N®-diphenylurea:alkanol reaction mixture.

U.S. Pat. No. 2,806,051 discloses the preparation of N-aryl monourethanes by reacting a primary amine, urea and an alcohol at a temperature greater than 100° C. The preferred ratio of amine to urea to alcohol is 1:1.2:2 and the preferred temperature range is from 125° C. to 160° C. In spite of extremely prolonged and commercially impractical reaction times (13 to 53 hours, average 36 hours), the yields are still unacceptably low, ranging from 7 percent to 75.6 percent and averaging only 34 percent, based upon the starting amine.

U.S. Pat. No. 2,677,698 describes the preparation of N-aryl monourethanes by reacting in a first step an aryl monoamine with urea. However, in this process, the aryl amine fails to react completely even over excessively long (up to 20 hours) reaction times. Thus the unreacted amine must be separated from the diarylurea intermediate. The large quantity of unreacted urea remaining in the diarylurea must also be removed before the purified diaryl urea is reacted with at least one mole of alcohol in the second step. From this second reaction mixture is obtained the N-aryl monourethane product plus free aryl monoamine which is then recycled. Because of the long reaction times, low yields, extensive purification steps and high recycle, this process is too expensive and, therefore, unsuitable for commercial exploitation.

U.S. Pat. No. 2,871,259 describes the preparation of unsubstituted carbamate esters by reaction of an alcohol with urea in a polyoxyalkylene glycol solvent. While high yields of unsubstituted carbamates may be obtained by recycle of the unreacted starting materials, the one-pass yields are only ca. 50 percent of theoretical. Furthermore, an attempt to increase the yield or reaction rate by raising the reaction temperature is limited b undesirable side reactions said to take place above 180° C. Thus, the reaction temperatures are limited to the preferred range of 140° C. to 150° C.

In spite of the foregoing attempts to prepare N-aryl urethanes, none of the prior art processes has been commercialized even for monourethanes. Therefore, it would not seem feasible to prepare N-aryl diurethanes by using aryl diamines as the starting materials in these processes. Indeed, the low yields of the prior art processes relative to monourethanes should be even lower for the preparation of di- or polyurethanes on both statistical as well as stereochemical grounds.

Furthermore, the presence of a difunctional amine (diamine) in the same reaction vessel with urea would be expected to lead to disubstituted ureas or polymeric products. For example, if 4,4'-diaminodiphenylmethane is used as the diamine in the process of U.S. Pat. No. 2,806,051, only intractable polyureas are formed, the starting materials apparently undergoing polymerization at the expense of urethane formation. It is also known that at temperatures greater than 140° C. aromatic amines react with the unsubstituted urethanes which are initially formed from urea and alcohol to form disubstituted ureas, as in the sequence below:

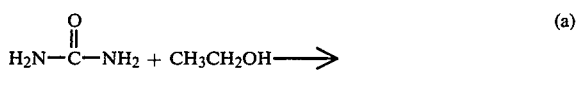

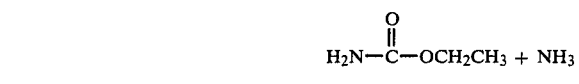

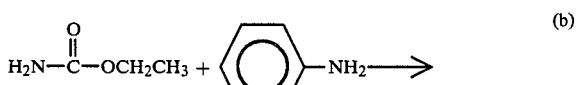

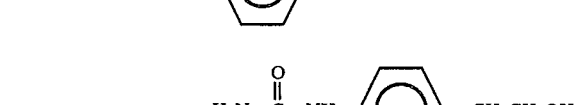

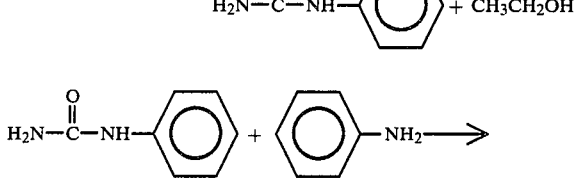

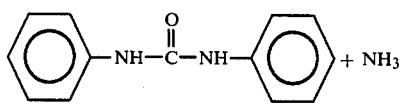

Thus, in the example above, benzenamine reacts with ethylcarbamate formed from urea and ethanol to form diphenyl urea. Houben-Weyl, *Methods of Organic Chemistry*, Vol. 8, page 161. Therefore, it is expected that the presence of (difunctional) diamines would result in polyureas:

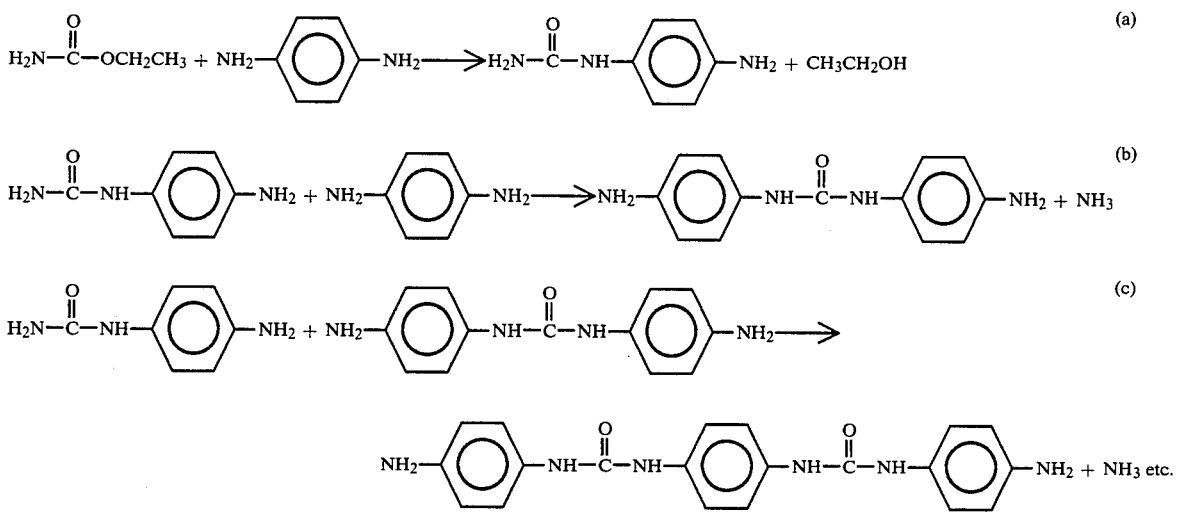

U.S. Pat. Nos. 2,181,663 and 2,568,885, for example, disclose the use of this process to prepare thermoplastic polyureas spinnable into fibers by reacting mixtures of diurethanes and diamines at temperatures from about 150° C. to 300° C.

In view of the prior art, therefore, it is indeed surprising that N-aryl di- or polyurethanes may be produced in one process step in high yield by reacting aromatic diamines with urea and alcohol at temperatures in the same range in which undesirable side reactions and polymerization, i.e., above 180° C., are known to occur. Furthermore, it has been unexpectedly discovered that rather than polymerization and undesirable side reactions expected when aromatic diamines are reacted at higher temperatures, that a sharp discontinuity in yield occurs between 180° C. and 190° C. wherein yields of di- and polyurethanes are generally above 90 percent.

SUMMARY OF THE INVENTION

It is an object of the subject invention to provide a process for the production of N-aryl di- or polyurethanes without the involvement of phosgene or carbon monoxide at any stage of the process. It is a further object of the invention to provide an economically viable means for the production of di- or polyurethanes using inexpensive and readily available starting materials. These and other objects of the invention, which will be apparent to one skilled in the art, are accomplished by reacting an aromatic di- or polyamine with urea and alcohol in a molar ratio of 1:1:10 to 1:5:30 at temperatures of from 185° C. to 300° C., preferably in the presence of suitable catalysts. The di- or polyurethanes thus produced have utility as pesticides and as chemical intermediates. They have particular utility in the preparation of di- or polyisocyanates through thermal cleavage.

DESCRIPTION OF THE PREFERRED EMBODIMENTS

In order to prepare the N-aryl di- or polyurethanes in accordance with the process of this invention, a primary aromatic di- or polyamine, or mixtures thereof, an alcohol, and urea are reacted in such quantities that the ratio of amino groups of the aromatic di- or polyamine to urea to hydroxyl groups of the alcohol is 1:0.8:5 to 1:10:100, preferably 1:0.9:5 to 1:7:50 and in particular, 1:1:10 to 1:5:30.

The alcohol which is in excess over the stoichiometric amount is utilized as a solvent for the reactants and the reaction is performed at temperatures of 185° C. to 300° C. and at normal pressures or under reduced or increased pressure. The most preferred temperature range is from about 185° C. to 230° C. One or more catalysts may be added to the reaction mixture in order to increase the reaction rate, improve the yield, or both. It has proven to be advantageous to remove the ammonia produced by the reaction as it is formed, for example, by means of distillation.

Unsubstituted or substituted primary aromatic di- or polyamines or their mixtures may be reacted with the urea and alcohol to prepare the di- or polyurethanes. Specific examples of aromatic di- or polyamines which are suitable include 1,3- and 1,4-diaminobenzene; 1,3-diaminobenzene substituted in the 2- and/or 4-position by nitro, methyl, ethyl, n-propyl, isopropyl, n-butyl, isobutyl, secondary butyl, tertiary butyl, methoxy, ethoxy, n-propoxy, isopropoxy, n-butoxy, isobutoxy, secondary butoxy, or tertiary butoxy groups, or with halogen atoms, preferably fluorine or chlorine; or 1,4-diaminobenzene similarly substituted in the 2-position; 1,5- and 1,8-diaminonaphthalene, 4,4'-diaminodiphenyl, 2,2'-, 2,4'-, and 4,4'-diaminodiphenylmethane and the corresponding isomer mixtures thereof, all of which may be substituted in the 2-position by nitro, methyl, ethyl, n-propyl, isopropyl, n-butyl, isobutyl, secondary butyl, tertiary butyl, methoxy, ethoxy, n-propoxy, isopropoxy, n-butoxy, isobutoxy, secondary butoxy, or tertiary butoxy groups, or with halogen atoms, preferably fluorine or chlorine; and polyphenylenepolymethylenepolyamines as well as mixtures of diaminodiphenylmethanes and polyphenylenepolymethylenepolyamines (polymeric MDA).

Preferably used as aromatic diamines, however, are 2,4- and 2,6-toluenediamine as well as the corresponding isomer mixtures; 2,2'- 2,4'- and 4,4'-diaminodiphenylmethane and the corresponding isomer mixtures; 1,5-diaminonaphthalene; and preferably mixtures of diaminodiphenylmethanes and polyphenylenepolymethylenepolyamines (polymeric MDA).

Any desired unsubstituted or substituted primary or secondary aliphatic alcohol or aromatic-aliphatic alcohol as well as mixtures thereof may be used as alcohols for the process according to this invention. Examples include primary aliphatic alcohols having 1 to 20 carbon atoms, preferably 1 to 10 carbon atoms, such as methanol, ethanol, propanol, n-butanol, isobutanol, 2- and 3-methylbutanol, neopentanol, pentanol, 2-methylpentanol, n-hexanol, 2-ethylhexanol, n-heptanol, n-octanol, n-nonanol, n-decanol, n-dodecanol, 2-phenylpropanol and benzyl alcohol; and secondary aliphatic and cycloaliphatic alcohols having 3 to 15 carbon atoms, preferably 3 to 6 carbon atoms, such as isopropanol, secondary butanol, secondary isoamyl alcohol, cyclopentanol, cyclohexanol, 2-, 3-, or 4-methylcyclohexanol and 4-tertiarybutyl cyclohexanol. Preferably used are methanol, ethanol, propanol, butanol, isobutanol, 2- and 3-methylbutanol, 2-ethylbutanol, pentanol, 2-methylpentanol, hexanol, 2-ethylhexanol, heptanol, octanol, and cyclohexanol.

As previously indicated, the reaction preferably is carried out with excess alcohol so that the alcohol functions both as a reaction component and simultaneously as a solvent. Instead of alcohol alone, however, mixtures of alcohols and other organic solvents which are inert under the reaction conditions may also be utilized as solvents.

According to the invention, the aromatic di- or polyurethanes, particularly the diurathanes, may be produced in the absence of catalyst since the uncatalyzed reaction normally takes place in economically acceptable reaction times and with good yields. In this manner, purification steps for removing the catalyst from the resultant end products are rendered unnecessary.

If it is desired to use catalysts in order to increase the rate of reaction, preferably at low temperatures, the catalyst should be used in quantities of 0.1 to 20 percent by weight, preferably 0.5 to 10 percent by weight, and, in particular, 1 to 5 percent by weight relative to the weight of the aromatic di- or polyamine. Suitable catalysts are inorganic or organic compounds containing one or more, preferably one, cation of metals of the groups IA, IB, IIA, IIB, IIIA, IIIB, IVA, IVB, VA, VB, VIB, VIIB, and VIIIB of the periodic system defined in accordance with the *Handbook of Chemistry and Physics*, (14th Edition, Chemical Rubber Publishing Company, 2310 Superior Avenue N.W., Cleveland, Ohio). These compounds include, for instance, halides such as chlorides and bromides, sulfates, phosphates, nitrates, borates, alkoxides, phenylates, sulfates, oxides, hydrated oxides, hydroxides, carboxylates, chelates, carbonates, and thio- or dithiocarbamates. Suitable, for example, are cations of any of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt, and nickel. Preferably used are the cations of lithium, calcium, aluminum, tin, bismuth, antimony, copper, zinc, titanium, Vanadium, chromium, molybdenum, manganese, iron, and cobalt. When economically feasible, the catalysts may also be used in the form of their hydrates or ammoniates.

Examples of typical catalysts include the following compounds: lithium methoxide, lithium ethoxide, lithium propoxide, lithium butoxide, sodium methoxide, potassium tertiarybutoxide, magnesium methoxide, calcium methoxide, tin(II) chloride, tin(IV) chloride, lead acetate, lead phosphate, antimony(III) chloride, antimony(V) chloride, aluminum isobutoxide, aluminum trichloride, bismuth(III) chloride, copper(II) acetate, copper(II) sulfate, copper(II) nitrate, bis(triphenylphosphineoxydo)copper(II) chloride, copper molybdate, silver acetate, gold acetate, zinc oxide, zinc chloride, zinc acetate, zinc acetylacetonate, zinc octoate, zinc oxalate, zinc hexylate, zinc benzoate, zinc undecyclenate, cerium(IV) oxide, uranyl acetate, titanium tetrabutylate, titanium tetrachloride, titanium tetraphenylate, titanium naphthenate, vanadium(III) chloride, vanadium acetylacetonate, chromium(III) chloride, molybdenum(VI) oxide, molybdenum acetylacetonate, tungsten(VI) oxide, manganese(II) chloride, manganese(II) acetate, manganese(III) acetate, iron(II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate, and nickel naphthenate, as well as their mixtures.

The reaction takes place at temperatures considerably higher than those recommended by the prior art processes, preferably from 185° C. to 250° C. and, more preferably, from 185° C. to 230° C., at pressures of from 0.1 bar to 120 bar, preferably 0.5 bar to 60 bar, and in particular from 1 bar to 40 bar. The reaction times which are appropriate for the corresponding temperature ranges are 0.1 hour to 50 hours, preferably 0.5 hour to 20 hours. With a given temperature, the reaction is preferably carried out under a pressure which allows the resultant ammonia to be fractionally distilled from the reaction mixture. The pressures and temperatures required may be taken from physical tables of data for ammonia and alcohols.

An effective way of preparing the aromatic di- or polyurethanes is to heat the reaction mixture to reflux at a pressure sufficient to maintain the reaction temperature at the desired value. The reaction vessel should be equipped with a device for separating the ammonia. While the ammonia produced can be separated after the reaction has been completed, it is preferable to separate it as it forms during the reaction. It may be advantageous, particularly in the case of the reaction of low molecular weight alcohols under pressure, to separate the ammonia by using a stripping agent such as nitrogen gas, which is inert under the reaction conditions.

A particularly advantageous method of preparing the aromatic di- or polyurethanes which as a rule results in a considerable reduction of the reaction time is described as follows. First, the primary aromatic di- or polyamines, the urea, and the alcohol are reacted in a ratio of amino groups to urea to alcohol of 1:1.5:2 to 1:3:10 preferably 1:1.5:4 to 1:2:8 for 0.5 hour to 3 hours, preferably 0.5 hour to 2 hours. In a second step, additional alcohol is added to the reaction mixture in an amount such that 10 to 30, preferably 15 to 30 moles of alcohol are present per mole of amino group of the amine, and such that the reaction is completed in a total time period of from 4 to 20 hours, preferably 4 to 10 hours. The di- or polyurethanes produced may then be isolated from the resulting reaction mixture either before or after removing the catalyst and filtering out solid materials. This ma be done, for example, by completely distilling off the alcohol and/or the solvent as well as any O-alkyl carbamates which are formed as byproducts; by partially distilling off the alcohol and crystallization; by crystallization alone; or by precipitation with or recrystallization from other solvents.

The following examples serve to illustrate the invention but do not serve to limit it in any way. The parts referred to in the examples are parts by weight. The compositions and structures were confirmed by elemental analysis and mass spectrometry as well as by their infrared and nuclear magnetic resonance spectra.

EXAMPLE 1

In a reaction vessel 10 parts (0.05 mole amino groups) of 4,4'-diaminodiphenylmethane, 15.2 parts (0.25 mole) urea and 195 parts (1.5 mole) n-octanol were heated to a reflux temperature of approximately 195° C. for five hours while the ammonia produced was simultaneously removed via distillation. The amine:urea:alcohol ratio was 1:2.5:15. The mixture was allowed to cool and 24.2 parts (0.0475 mole, 94.0 percent theory, m.p. 118°–119° C.) of 4,4'-bis(octoxycarbonylamino)diphenylmethane was removed by filtration.

Example 2

In a reaction vessel 5 parts (0.025 mole amino groups) 4,4'-diaminodiphenylmethane, 6.1 parts (0.10 mole urea) and 46 parts (0.62 moles) n-butanol were refluxed at a pressure of 7 to 8 bar to maintain the reaction temperature at approximately 200° C. The ratio of reactants was 1:4:24.6. Twenty-five liters per hour of nitrogen per liter of reaction mixture was utilized to strip the ammonia formed during the reaction. The product was allowed to cool, depressurized and the solvent concentrated resulting in crystallization of 8.4 parts (0.0211 mole, 83.6 percent theory, m.p. 91°–95° C.) of 4,4'-bis(-butoxycarbonylamino)diphenylmethane. In addition to the desired product, recyclable 4-amino-4'-(butoxycarbonylamino)diphenylmethane is present in the mother liquor.

p COMPARISON EXAMPLE C-1

The process of Brockway, 2,806,051, was utilized but a diamine was substituted for the monoamine. Ten parts (0.10 mole amino groups) 4,4'-diaminodiphenylmethane, 7.3 parts (0.12 mole) urea, and 15 parts (0.20 mole) n-butanol were heated to reflux at 120° C. to 122° C. The amine:urea:alcohol ratio was 1:1.2:2. After approximately 45 minutes the reaction mixture appeared cloudy. As the reaction progressed, increasingly larger amounts of an insoluble solid precipitated over the course of 90 hours. The solid was determined to be a polyurea by infrared spectroscopy.

COMPARISON EXAMPLE C-2

The procedure of Comparison Example C-1 was followed but with 5 parts (approximately 0.025 mole amino groups) polymeric MDA, 4 parts (0.067 mole) urea, and 53 parts (0.715 mole) n-butanol. The amine:urea:alcohol ratio was 1:2.7:28.6. After four hours, a considerable amount of colorless insoluble solid had formed which increased until stirring was no longer possible. Infrared spectroscopy confirmed the structure as a polyurea.

Examples 1 and 2 show the high yields which are typically generated when the process of the subject invention, i.e., reactant ratios of 1:1:10 to 1:5:30and high temperature, i.e., preferably 185° C. to 230° C., are utilized. It should be noted that the actual urethane yield of both Examples 1 and 2 is higher than that stated as the yields do not take into account either the monourethanes formed which may be advantageously recycled, nor minor amounts of product remaining dissolved in the mother liquor.

Comparative Examples C-1 and C-2 show that the literature predictions regarding the use of aromatic diamines in prior art processes are justified in that insoluble polymerization products (polyureas) are formed at the expense of di- or polyurethane formation. Example C-2 shows that within the temperature range of the prior art not even a ratio of reactants that is within the preferred range of the subject invention is helpful in preventing formation of undesirable side reactions leading to intractable polyureas. The results of these examples (1, 2, C-1, C-2) are found in Table I along with those of corresponding prior art processes. Yields of the examples of the subject invention which are predicted on the basis of prior art yields are also included.

TABLE I

| Example | Amine | Alcohol | Amino Group/ Urea/Alcohol Mole Ratio | Reaction Temp., °C. | Reaction Time, Hrs. | Di- or Poly- Urethane Yield, % |
|---|---|---|---|---|---|---|
| 1 | 4,4'-methylenedianiline | n-octanol | 1/2.5/15 | 195 | 5 | 94.0[5] |
| 2 | " | n-butanol | 1/4/24.6 | 200 | — | 86.3[3] |
| C-1 | " | " | 1/1.2/2 | 120–122 | 90 | polyurea |
| C-2 | Polymeric MDA | " | 1/2.7/28.6 | 120–122 | 4 | polyurea |
| 3 | 2,4-toluenediamine | n-octanol | 1/5/15 | 200 | 5 | 92.0[4] |
| 4 | " | " | " | 190 | 5 | 91.0 |
| C-3 | " | " | " | 180 | 5 | 70.0 |
| C-4 | " | " | " | 170 | 5 | 72.0 |
| C-5 | " | " | " | 160 | 5 | 71.0 |
| C-6 | " | " | 1/2.5/5 | 150 | 5 | 26.0 |
| C-7 | " | " | " | 160 | 5 | 44.0 |
| 5 | " | cyclohexanol[1] | 1/1.2/10 | 200 | 10 | 48.1[2,5] |
| Brockway I | Aniline | n-butanol | 1/1.2/2 | 123–144 | 22 | 75.6 |
| Brockway III | " | n-octanol | " | 150–160 | 13 | 49.4 |

TABLE I-continued

| Example | Amine | Alcohol | Amino Group/Urea/Alcohol Mole Ratio | Reaction Temp., °C. | Reaction Time, Hrs. | Di- or Poly-Urethane Yield, % |
|---|---|---|---|---|---|---|
| Brockway V | " | cyclohexanol | " | 140–147 | 53 | 13.6 |

[1] Secondary alcohol
[2] 98.1% diamine reacted; total urethane group yield 73.1%
[3] *Expected yield (from Brockway Example I) is 57.2%
[4] *Expected yield (from Brockway Example III) is 24.4%
[5] *Expected yield (from Brockway Example IV) is 1.8%
[6] Total urethane group yield is greater
*Statistical yield based upon Brockway process (monoamine v. diamine). Expected decreases due to steric hindrance and side reactions expected at higher process temperature not considered.

EXAMPLE 3

In a reaction vessel, 3.05 parts (0.05 mole amino groups) 2,4-toluenediamine, 15 parts (0.25 mole) urea and 97.5 parts (0.75 mole) n-octanol were heated for five hours at a slight pressure sufficient to maintain a reaction temperature of approximately 200° C. while continuouslY removing ammonia by distillation. The reaction mixture was then subjected to fractional distillation in vacuo to a pot temperature of 180° C. The resulting solution contained 10.0 parts (0.023 mole, 92 percent theory) of 2,4-bis(octoxycarbonylamino)toluene as determined by HPLC, m.p. 68° C.–70° C. (from cyclohexane).

EXAMPLE 4

The procedure of Example 3 was followed but at a lower pressure sufficient to maintain a reaction temperature of 190° C. The yield of 2,4-bis(octoxycarbonylamino)toluene is 9.9 parts (0.0228 mole, 91 percent theory).

COMPARISON EXAMPLE C-3

The procedure of Examples 3 and 4 was followed but the pressure lowered further to maintain a reaction temperature of 180° C. The yield is only 7.6 parts (0.0175 mole, 70 percent theory).

COMPARISON EXAMPLES C-4 and C-5

The process of Examples 3, 4, and 5 was used but with the pressure adjusted to maintain temperatures of 170° C. and 160° C., respectively. The yields were 7.8 parts (0.195 mole, 72 percent theory) and 7.7 parts (0.192 mole, 71 percent theory), respectively.

Examples 3 and 4 again illustrate the high yields which may be obtained with the process of the subject invention. It should b noted that these reported yields do not include additional monourethanes formed. These monourethanes may be recycled resulting in even higher overall yields. Examples C-3, C-4, and C-5 illustrate, when compared with Examples 3 and 4, the sharp discontinuity in yield caused by reaction temperatures in excess of 180° C. At 190° C. there is an actual 20 percent increase in yield over the yield at the lower range of 160° to 180° C. The yield at the higher temperature, therefore, is approximately 28 percent higher on a relative basis. This significantly higher yield presents obvious economic advantages to the process of the subject invention.

COMPARISON EXAMPLES C-6 AND C-7

In a reaction vessel, 9.15 parts (0.150 mole amino groups) 2,4-toluenediamine, 22.5 parts (0.375 mole) urea, and 97.5 parts (0.75 mole) n-octanol were reacted for five hours while continuously removing ammonia by distillation. Reactant ratios are within the range suggested by Brockway (1:2.5:5). The pressure was adjusted so as to maintain reaction temperatures of 150° C. and 160° C., respectively. Yields were 16.9 parts, 26 percent theory; and 28.6 parts, 44 percent theory, respectively. Reactions at lower temperatures result in still lower yields. The low yields of diurethanes using the reactant ratios of the prior art is believed to be caused by polymerization to polyureas at the expense of urethane formation.

The presence of polyureas in these amounts would render continuous production processes much more expensive or totally inoperative owing to the need to separate the solid and relatively insoluble polyureas in order to prevent clogging or build-up of residue in the reaction vessels, distillation equipment, etc.

Comparison Examples C-6 and C-7 illustrate the criticality of both the temperature range as well as the reactant ratios of the subject invention. As expected, the yield of diurethane product in Comparison Examples C-6 and C-7 which use Brockway conditions is less than that of the monourethane products as produced by Brockway. When the yields of Comparison Examples C-6 and C-7 are averaged so as to be comparable to the prior art monourethane example, an average yield of 35 percent results; considerably lower than the corresponding value of 49.4 percent from Brockway (Example III, column 3, of U.S. Pat. No. 2,806,051) which was performed at 150° C. to 160° C. Comparison Example C-5 and Comparison Example C-7, which were performed at the same temperature, serve to illustrate the improvement in yield obtained when reactant ratios taught by the subject invention are used (20 percent absolute, 61 percent relative). However, even this improvement, without the additional improvement produced by operation at temperatures greater than 180° C., would not be enough to make the process commercially useful.

EXAMPLE 5

In a reaction vessel, 12.2 parts (0.20 mole amino groups) 2,4-toluenediamine, 14 parts (0.233 mole) urea and 200 parts (2 moles) cyclohexanol are reacted for 10 hours at a reflux temperature of approximately 200° C., this reflux temperature having been obtained by maintaining the pressure at 2 to 3 bar. Ammonia is removed by distillation with the aid of 25 liters per hour of nitrogen per liter of reaction mixture as a stripping agent. After cooling, the reaction mixture contains 18 parts (0.0415 mole, 48.1 percent theory) of 2,4-bis(cyclohexoxycarbonylamino)toluene and 12.4 parts (0.5 mole, 50.0 percent theory) of a mixture of 2-amino-4-(cyclohexoxycarbonylamino)toluene and 4-amino-2-(cyclohexoxycarbonylamino)toluene which is capable of being recycled. The total urethane group yield based on amino groups is 73.1 percent.

Example 5 illlustrates the utility of the process of the subject invention for the preparation of n-aryl urethanes using a secondary alcohol as the esterifying alcohol. In spite of the lower reactivity of the secondary alcohol, the diurethane yield after ten hours is more than acceptable; the total urethane group yield based upon amino groups is good; and the reactivity of the diamine (98.1 percent reacted) is excellent. In contrast, the prior art (Brockway, Example V) shows a yield of only 13.6 percent after 53 hours, a time too long to be commercially useful.

EXAMPLE 9

In a reaction vessel, 12.2 parts (0.20 mole amino groups) 2,4-toluenediamine, 32 parts (0.53 mole) urea, and 104 parts (0.80 mole) n-octanol were heated to reflux at approximately 195° C. for 1 hour, following which an additional 416 parts (3.2 mole) n-octanol was added. The amine:urea:alcohol ratio was 1:2.7:20. During the next 4 hours, ammonia was removed continuously by distillation. After completion of the reaction, excess n-octanol and carbamic octyl ester were removed by fractional distillation in vacuo to a pot temperature of 190° C. 40.2 parts (0.0926 mole, 92.6 percent theory) of 2,4-bis(octoxycarbonylamino)toluene was found in the distillation residue by HPLC.

EXAMPLE 7

In a reaction vessel, 6.1 parts (0.10 mole amino groups 2,4-toluenediamine, 15 parts (0.25 mole) urea, and 18.4 parts (0.40 mole) ethanol were heated to reflux at a pressure of 24 to 25 bar so as to maintain the reaction temperature at approximately 195° C. After 45 minutes, an additional 74 parts (1.60 mole) ethanol were added. Ammonia was separated continuously by distillation using 30 liters of nitrogen per hour a stripping agent. The reaction mixture contained 11.1 parts (0.0417 mole, 83.5 percent theory) of 2,4-bis(ethoxycarbonylamino)-toluene and 1.4 parts (14.4 percent theory based on diamine, 7.2 percent based on amino groups) 2-amino-4-(ethoxycarbonylamino)toluene and 4-amino-2-(ethoxycarbonylamino)toluene. Reactivity of the diamine is 97.9 percent, and urethane group yield based upon amino groups reacted is in excess of 90.7 percent.

Examples 6 and 7 illustrate the use of the two-step procedure for production of di- or polyurethanes.

EXAMPLE 8

In a reaction vessel, 8 parts (0.10 mole amino groups) of 1,5-diaminonaphthalene, 18 parts (0.30 mole) urea and 150 parts (1.15 mole) n-octanol were heated to reflux at approximately 195° C. for ten hours, the ammonia continuously separated by distillation. Upon cooling, a mixture of unreacted 1,5-diaminonaphthalene and 1,5-(octoxycarbonylamino)naphthalene crystallized. Following recrystallization from ethyl acetate, 15 parts (0.0319 mole, 64.3 percent theory, m.p. 69° C.-71° C.) are obtained. The mother liquor also contains appreciable amounts of the monourethane 1-amino-5-(octoxycarbonylamino)naphthalene.

EXAMPLE 9

Example 11 was repeated with the addition of 0.1 part (0.0019 mole) sodium methoxide as a catalyst. 18.7 parts (0.040 mole, 78.6 percent theory, m.p. 71° C. to 72° C.), 1,5-(octoxycarbonylamino)naphthalene were obtained.

Examples 8 and 9 illustrate the greater effectiveness of the catalytic preparation of N-aryl diurethanes. Using a difficultly reactive amine, the addition of 0.1 part of catalyst to the reaction mixture increased the yield from 64.3 percent to 78.6 percent, a relative increase of 22 percent. Furthermore, as can be seen from the narrower melting point range, the product from the catalyzed reaction represents a higher purity product. The efficiency of various catalysts is shown in Examples 10-14 and Table II. It should be borne in mind that in these examples a reactant ratio outside of the range of the subject invention was deliberately chosen in order to demonstrate the utility of the catalyst even under less than ideal conditions.

COMPARISON EXAMPLE C-8

In a reaction vessel, 6.1 parts (0.10 mole amino groups) 2,4-toluenediamine, 12 parts (0.2 mole) urea and 18.4 parts (0.4 mole) ethanol, a reactant ratio ©f 1:2:4, was refluxed at a pressure of 17 to 18 bar in order that the reaction temperature be maintained at approximately 180° C. Nitrogen at the rate of 5 liters per hour per liter of reaction mixture was used as a stripping agent to assist in the removal of ammonia by distillation. After five hours the reaction mixture is shown by HPLC to contain 6.2 parts (0.0233 mole, 46.6 percent theory based on diamine present), 2,4-bis(ethoxycarbonylamino)toluene. 1.3 parts 2,4-toluenediamine remain unreacted. The yield of diurethane based upon 2,4-toluenediamine reacted, therefore, was 58.8 percent with a volume time yield of 34 grams per liter per hour.

EXZAMPLES 10-14

The process of Comparison Example C-8 was duplicated but with the addition of 0.1 part of representative catalyst. The catalyst used, yields, and reaction times are summarized in Table II.

TABLE II

| Example No. | Catalyst | Diamine Conversion % | Time h. | Volume-Time Yield g/l/h | Diurethane Yield % |
| --- | --- | --- | --- | --- | --- |
| C-8 | — | 46.6 | 5 | 34.0 | 58.8 |
| 10 | Cobalt(II) acetate | 83.2 | 5 | 38.8 | 64.0 |
| 11 | Manganese(II) acetate | 81.9 | 5 | 39.3 | 65.8 |
| 12 | Vanadium trichloride | 96.1 | 3 | 55.1 | 47.2 |
| 13 | Zinc acetate | 78.5 | 3 | 65.1 | 68.3 |
| 14 | Iron(II) acetate | 77.8 | 3 | 63.5 | 67.2 |

The embodiments of the invention in which an exclusive privilege or property is claimed are defined as follows:

1. A process for the preparation of N-aryl di- or polyurethanes, comprising reacting at a temperature of from about 190° C. to 300° C. an aromatic primary amine selected from the group consisting of
   (a) aromatic diamines
   (b) aromatic polyamines, and
   (c) mixtures thereof;

with urea and a primary or secondary aliphatic, cycloaliphatic, or arylaliphatic alcohol wherein the mole ratio of amino groups to urea to hydroxyl groups is in the range of 1:0.8:5 to 1:10:100; and separating said di- or polyurethanes from unreacted starting materials and partly reacted starting materials.

2. A process for the continuous preparation of N-aryl di- or polyurethanes, comprising reacting at a temperature of from about 190° C. to 300° C. an aromatic primary amine selected from the group consisting of
   (a) aromatic diamines
   (b) aromatic polyamines, and
   (c) mixtures thereof;
with urea and a primary or secondary aliphatic, cycloaliphatic, or arylaliphatic alcohol wherein the mole ratio of amino groups to urea to hydroxyl groups is in the range of 1:0.8:5 to 1:10:100, wherein the temperature of the reaction is in the range of from about 190° C. to 300° C.; and wherein unreacted starting materials, and partly reacted starting materials are recycled.

3. A process for the preparation of N-aryl di- or polyurethanes, comprising reacting, in the first step, from about 0.5 to 3 hours, an aromatic primary amine selected from the group consisting of
   (a) aromatic diamines
   (b) aromatic polyamines, and
   (c) mixtures thereof;
with urea and a primary or secondary aliphatic, cycloaliphatic, or arylaliphatic alcohol, wherein the ratio of amino groups to urea to hydroxyl groups is in the range of 1:1.5:2 to 1:3:8 and wherein the temperature of the reaction is in the range of from about 190° C. to 250°C.; and adding, in the second step, sufficient alcohol to change the amino group to hydroxyl group ratio to the range of 1:10 to 1:30 and reacting to the desired degree of reaction completion and separating said di- and polyurethanes from unreacted starting materials and partly reacted starting materials.

4. The process of claims 1, 2, or 3 further comprising the use of a catalytically effective amount of a metal containing compound wherein the metal is selected from the metals of groups IA, IB, IIA, IIB, IIIA, IIIB, IVA, IVB, VA, VB, VIB, VIIB, and VIIIB of the periodic system.

5. The process of claims 1, 2, 3, or 4 wherein said aromatic amine comprises one or more of: 2,4- toluenediamine, 2,6 -toluenediamine, 4,4'-diaminodiphenylmethane, 2,4'-diaminodiphenylmethane, 2,2'-diaminodiphenylmethane, 1,5-napthalenediamine, and polyphenylenepolymethylenepolyamine.

6. The process of claims 1, 2, 3, or 4 wherein said aromatic amine is polymeric MDA.

7. The process of claims 1, 2, 3, or 4 wherein said alcohol is selected from the group consisting of methanol, ethanol, propanol, butanol, isobutanol, 2- and 3-methylbutanol, 2-ethylbutanol, pentanol, 2-methylpentanol, hexanol, 2-ethylhexanol, heptanol, octanol, cyclohexanol, and mixtures thereof.

8. The process of claims 1, 2, 3, or 4 wherein ammonia formed during the reaction is removed continuously.

9. The process of claim 1 wherein the reaction temperature is from about 190° C. to 250° C.

10. A process for the preparation of N-aryl di- or polyurethane product, comprising reacting an aromatic amine having two or more primary amino groups with urea and a primary or secondary aliphatic, cycloaliphatic, or arylaliphatic alcohol in an amino group to urea to alcohol molar ratio of from 1:0.8:5 to 1:10:100, at a temperature of from 180° C. to 300° C., in the presence of an effective amount of a metal cation containing catalyst wherein said metal cation is a metal cation from groups IA, IB, IIA, IIB, IIIA, IIIB, IVA, IVB, VA, VB, VIB, VIIB or VIIIB of the periodic table.

11. The process of claim 10 wherein said aromatic amine is selected from the group consisting of 2,4- and 2,6-toluenediamine, 2,2'-2,4'-, and 4,4'-diaminodiphenylmethane, polyphenylenepolymethylenepolyamine, and mixtures thereof, and wherein said alcohol is selected from the group consisting of methanol, ethanol, n-propanol, isopropanol, n-pentanol, 2- and 3-methylbutanol, 2-ethylbutanol, n-pentanol, 2-methylpentanol, n-hexanol, 2-ethylhexanol, n-heptanol, n-octanol, cyclohexanol, and mixtures thereof.

12. The process of claim 10 wherein said metal cation is a metal cation selected from the group consisting of the cations of lithium, calcium, aluminum, tin, bismuth, antimony, copper, zinc, titanium, vanadium, chromium, molybdenum, manganese, iron, and cobalt.

13. The process of claim 4 or 12 wherein the catalyst is selected from the group consisting of sodium methoxide, cobalt(II) acetate, manganese(II) acetate, vanadium trichloride, zinc acetate and iron(II) acetate.

14. The process of claim 12 wherein said aromatic amine is selected from the group consisting of 2,4- and 2,6-toluenediamine, 2,2'- 2,4'-, and 4,4'-diaminodiphenylmethane, polyphenylenepolymethylenepolyamine, and mixtures thereof, and wherein said alcohol is selected from the group consisting of methanol, ethanol, n-propanol, isopropanol, n-pentanol, 2- and 3-methylbutanol, 2-ethylbutanol, n-pentanol, 2-methylpentanol, n-hexanol, 2-ethylhexanol, n-heptanol, n-octanol, cyclohexanol, and mixtures thereof.

15. A two-step prodess for the preparation of N-aryl di- or polyurethanes comprising:
   (1) reacting an aryl primary amine having two or more primary amino groups with urea and a primary or secondary aliphatic, cycloaliphatic, or arylaliphatic alcohol in an amino group to urea to alcohol mole ratio of from 1:1.5:2 to 1:3:10 in the presence of an effective amount of a metal cation containing catalyst wherein said metal cation is a metal cation from groups IA, IB, IIA, IIB, IIIA, IIIB, IVA, IVB, VA, VB, VIB, VIIB or VIIIB of the periodic table, at a reaction temperature of from about 180° C. to 300° C. for a period of from 0.5 hour to 3 hours, and
   (2) adding sufficient alcohol to increase the alcohol to amino group ratio to a mole ratio of from 15:1 to 30:1,
such that the total reaction period including steps 1 and 2 is from 4 to 20 hours.

16. The process of claim 15 wherein said aromatic amine is selected from the group consisting of 2,4- and 2,6-toluenediamine, 2,2'- 2,4'-, and 4,4'-diaminodiphenylmethane, polyphenylenepolymethylenepolyamine, and mixtures thereof, and wherein said alcohol is selected from the group consisting of methanol, ethanol, n-propanol, isopropanol, n-pentanol, 2- and 3-methylbutanol, 2-ethylbutanol, n-pentanol, 2-methylpentanol, n-hexanol, 2-ethylhexanol, n-heptanol, n-octanol, cyclohexanol, and mixtures thereof.

17. The process of claim 15 wherein said metal catio is a metal cation selected from the group consisting of the cations of lithium, calcium, aluminum, tin, bismuth, antimony, copper, zinc, titanium, vanadium, chromium, molybdenum, manganese, iron, and cobalt.

18. The process of claim 10 wherein said di- or polyurethane product is separated from unreacted starting materials and said starting materials are recycled.

* * * * *